(12) United States Patent
Sofranko

(10) Patent No.: US 11,648,328 B2
(45) Date of Patent: May 16, 2023

(54) DISINFECTING DEVICE

(71) Applicant: EcoCatalytic Inc., Weston, MA (US)

(72) Inventor: John A. Sofranko, Weston, MA (US)

(73) Assignee: ECOCATALYTIC INC., Weston, MA (US)

( * ) Notice: Subject to any disclaimer, the term of this patent is extended or adjusted under 35 U.S.C. 154(b) by 0 days.

(21) Appl. No.: 17/915,012

(22) PCT Filed: Mar. 26, 2021

(86) PCT No.: PCT/US2021/024276
§ 371 (c)(1),
(2) Date: Sep. 27, 2022

(87) PCT Pub. No.: WO2021/202258
PCT Pub. Date: Oct. 7, 2021

(65) Prior Publication Data
US 2023/0118959 A1    Apr. 20, 2023

Related U.S. Application Data

(60) Provisional application No. 63/001,260, filed on Mar. 28, 2020.

(51) Int. Cl.
*A61L 2/26* (2006.01)
*A61L 2/20* (2006.01)
(Continued)

(52) U.S. Cl.
CPC ............. *A61L 2/26* (2013.01); *A01N 35/02* (2013.01); *A61L 2/18* (2013.01); *A61L 2/204* (2013.01); *A61L 2/206* (2013.01); *B01J 23/34* (2013.01); *B01J 23/835* (2013.01); *B01J 23/8892* (2013.01); *A61L 2101/02* (2020.08);
(Continued)

(58) Field of Classification Search
CPC ... A61L 2/18; A61L 2/26; A61L 2/204; A61L 2/206; A61L 2202/11; A61L 2202/122; A61L 2202/123; A61L 2202/13; A01N 35/02; B01J 23/34; B01J 23/835; B01J 23/8892
See application file for complete search history.

(56) References Cited

U.S. PATENT DOCUMENTS 6,481,219 B2   11/2002   Palermo
6,603,039 B1    8/2003   Ebner et al.
(Continued)

OTHER PUBLICATIONS

International Preliminary Report on Patentability and Written Opinion for International Application No. PCT/US2021/024276, dated Sep. 29, 2022, 6 pages.
(Continued)

*Primary Examiner* — Sean E Conley
(74) *Attorney, Agent, or Firm* — RatnerPrestia

(57) ABSTRACT

A device for production and use of a disinfectant. The device may be used to disinfect materials or objects exposed to viruses and/or bacteria. In particular, the device is capable of converting at least one first reagent such as an alcohol and at least one second reagent including an oxidant into an active disinfectant agent. A catalytic system is incorporated into the reaction vessel to produce the active disinfectant as needed for the disinfection process.

29 Claims, 2 Drawing Sheets

(51) Int. Cl.
    *A61L 2/18*           (2006.01)
    *B01J 23/34*         (2006.01)
    *B01J 23/835*      (2006.01)
    *A01N 35/02*       (2006.01)
    *B01J 23/889*      (2006.01)
    *A61L 101/02*      (2006.01)
    *A61L 101/36*      (2006.01)

(52) U.S. Cl.
    CPC ........ *A61L 2101/36* (2020.08); *A61L 2202/11* (2013.01); *A61L 2202/122* (2013.01); *A61L 2202/123* (2013.01); *A61L 2202/13* (2013.01)

(56) References Cited

U.S. PATENT DOCUMENTS

| | | |
|---|---|---|
| 8,017,082 B2 | 9/2011 | McSherry et al. |
| 9,000,246 B2 | 4/2015 | Snead et al. |
| 2007/0104610 A1* | 5/2007 | Houston ................... A61L 2/14 |
| | | 373/18 |
| 2012/0031431 A1 | 2/2012 | Carlson et al. |
| 2014/0275679 A1 | 9/2014 | Sofranko |

OTHER PUBLICATIONS

International Search Report and Written Opinion for International Application No. PCT/US2021/024276, dated Jun. 14, 2021, 6 pages.

\* cited by examiner

DISINFECTING DEVICE

CROSS REFERENCE TO RELATED APPLICATIONS

This application is the U.S. National Phase of PCT/US2021/024276, filed Mar. 26, 2021, which claims priority to and benefit of U.S. Provisional Patent Application No. 63/001,260, filed on Mar. 28, 2020, the disclosure of each of which are incorporated herein by reference in their entireties for all purposes.

FIELD OF THE INVENTION

The invention is related to disinfecting devices capable of producing disinfectants on an as-needed basis that can disinfect objects exposed to certain viruses or bacteria.

BACKGROUND OF THE INVENTION

Pan epidemics and possible bio terrorism are a reality of current world heath conditions. While self-isolation and social distancing can be effective measures to inhibit the spread of infectious diseases, common practices such as mail and parcel delivery can jeopardize their success. The disinfection of mail and deliveries has been practiced since the fourteenth century when methods were first introduced by society to limit the spread of the bubonic plague. In the modern times, high-energy beam of ionizing radiation that kills bacteria has been broadly utilized to disinfect mail, in particular, mail deliveries to Washington, DC. However, ion beam systems are only safe when used under highly controlled condition and by skilled technicians. Ethylene oxide is also widely used as a disinfectant to electronic equipment for use in the health care profession since it is compatible with many materials that cannot tolerate or are degraded by radiation and moist heat sterilization. While this compound is highly effective as a disinfectant, it is also very toxic to humans, and in fact is considered to be a carcinogen by the US Environmental Protection Agency, so storage of tanks in a hospital environment present a safety risk. The manufacture and transportation of ethylene oxide also presents many safety risks. In addition, possible shortages of ethylene oxide may also pose a risk to hospitals and other facilities needing ethylene oxide to sterilize equipment and supplies.

Thus, there is a need for a device that is capable of producing a suitable disinfectant or sterilization composition in-site and in situ that can not only produce such a disinfectant safely and as needed, but can disinfect an object that may have been exposed to a virus or bacteria while minimizing human exposure to the disinfectant composition and its spent by-products.

SUMMARY OF THE INVENTION

Disclosed is a device for production and use of a disinfectant. The device may be used to disinfect materials or objects exposed to viruses and/or bacteria. In particular, the device is capable of converting at least one first reagent such as an alcohol and at least one second reagent including an oxidant into an active disinfectant agent. Key to this invention is a catalytic system, incorporated into the reaction vessel, that produces the active disinfectant as needed for the disinfection process.

A disinfection device is provided. The device includes a disinfection vessel which is configured to receive material to be disinfected. The device also includes a reagent vessel in fluid communication with the disinfection vessel. The reagent vessel is configured to contain at least one first reagent, which may include at least one alcohol. The reagent vessel also has at least one inlet that is configured to introduce at the least one first reagent including at least one alcohol into the reagent vessel. Also part of the disinfection device is a reactor vessel that is in fluid communication with the reagent vessel and also in fluid communication with the disinfection vessel. The reactor vessel is configured to receive at least one catalyst. The at least one catalyst in the reaction vessel includes at least one metal selected from transition metals, lanthanide metals and combinations thereof. The reactor vessel further has at least one inlet configured to introduce at least one second reagent into the reactor vessel. The second reagent includes an oxidant. The reactor vessel is also in fluid communication with a collection vessel and the collection vessel has at least one outlet.

In operation, the at least one first reagent that includes an alcohol and the at least one second reagent that includes an oxidant are contacted with the at least one catalyst in the reactor vessel and thus catalytically reacted together. The catalytic reaction forms an active disinfecting agent that includes at least one of aldehydes, carboxylic acids, oxiranes, carbon monoxide, or mixtures thereof. The active disinfecting agent then is dispersed to the disinfection vessel and contacted with the material to be disinfected, thus providing a disinfected material and a spent disinfecting agent. The spent disinfecting agent is collected in the collection vessel and removed from the disinfection device via the at least one outlet of the collection vessel.

DETAILED DESCRIPTION OF THE INVENTION

A device for the production of a disinfectant to disinfect objects or materials is provided. In particular, the device is capable of producing, by a catalytic or electrogenerative process utilizing a catalyst, a disinfectant that includes aldehydes, such as acetaldehyde. Acetaldehyde may be an effective disinfectant on a broad range of harmful biological agents such as bacteria, fungi, viruses and even bacterial spores. In particular, it may be effective to disinfect an enveloped virus such as the virus responsible for the COVID-19 sickness, SARS-CoV-2 and mutated variants thereof.

As used herein the term "disinfecting agent" means a compound and/or composition capable of being used to eliminate microorganisms and/or viruses to a degree that they are incapable or less capable of causing an infection or sickness.

Acetaldehyde may be an effective disinfectant for enveloped viruses, such as the SARS-CoV-2 virus. Importantly, an active disinfecting agent including acetaldehyde can be produced on an as-needed basis in the disclosed disinfecting device. In particular, the active disinfecting agent including acetaldehyde may be produced from very a common and widely available safe liquid, ethanol, or a mixture of ethanol and water, commonly available as distilled spirits by the disclosed disinfecting device. One aspect of this invention is a catalytic system, incorporated into the device, that is capable of producing an active disinfecting agent including acetaldehyde as needed for use in the disclosed disinfection device. In addition, the disclosed device is capable not only of producing the disinfectant composition catalytically on an as-needed basis, but also of preventing or minimizing exposure of the surrounding environment to the disinfectant composition before, during, and after a material is disinfected. Further, the disclosed disinfecting device is capable of catalytically producing the active disinfecting agent at mild temperatures and at pressures ranging from below atmospheric to atmospheric, or above.

Figure 1:
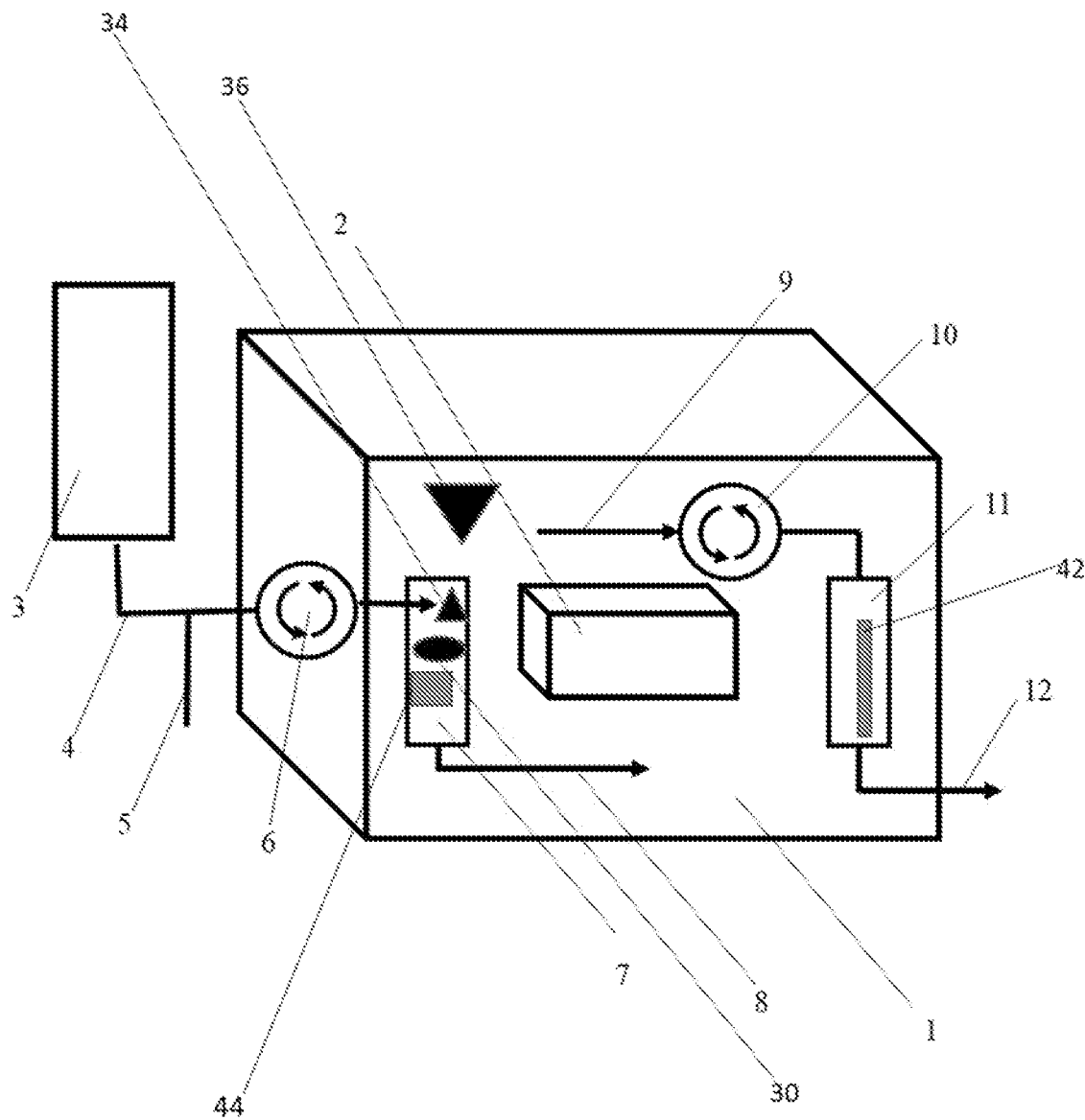
FIG. 1 shows a schematic of a device according to an embodiment of the invention.

In some embodiments, such as depicted in FIG. 1, the invention includes the use of any disinfectant made by the catalytic conversion of a feed stream including at least one alcohol to compounds that are effective as disinfectants to biological health hazards. This disclosure is also directed to the use of any disinfectant made by the catalytic conversion of a feed stream including at least one alcohol to compounds that are effective as disinfectants to biological health hazards whereby the catalytic reaction takes place within the device and on demand to produce the active disinfecting agent. This disclosure is directed to the use of the disinfecting device as disclosed herein for the disinfection of materials, in particular, such materials contaminated by enveloped viruses such as the virus responsible for the COVID-19 sickness, SARS-CoV-2 and mutated variants thereof. The present invention includes a high yield catalyst for the conversion of ethanol, or any alcohol, to an aldehyde such as acetaldehyde containing product, shown below as reaction (1). Concentrations of alcohols may be 0.01-100% of the feed. The feed may be diluted with water and, as such, common vodka or other spirits may be an effective feed (as the first reactant) to the device. This feature is particularly important for the safe use of this device in the home environment because these common alcoholic beverages may be considered essential items and can still be purchased under government imposed lock-down orders.

As noted above, a non-limiting example of a reaction that may take place catalytically in the disinfection device is shown below in Equation 1.

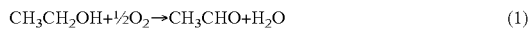

$$CH_3CH_2OH + \tfrac{1}{2}O_2 \rightarrow CH_3CHO + H_2O \quad (1)$$

As is known in the art, other alcohols used as the starting material will result in the production of different aldehydes. In addition, side reactions may take place such that the reaction produces other compounds such as but not limited to formaldehyde, acetic acid, formic acid, propionic acid, carbon monoxide, ethylene oxide or higher molecular weight aldehydes.

Exemplary Disinfecting Device

FIG. 1. illustrates a schematic diagram of a disinfection device according to an embodiment of the invention. A disinfection vessel 1 is configured to contain material 2 that needs to be disinfected. A reagent vessel 3 may be outside or inside the disinfection vessel 1 and is configured to accept and contain a first reagent(s) to feed to a reactor vessel 7. This reagent, or mixture of reagents, is transferred via line 4 and an optional pump or circulating device 6 to the reactor vessel 7. The reactor vessel has at least one other inlet 5. As shown in FIG. 1, the inlet 5 may be placed before the pump 6 or the inlet 5 may be placed such that it enters after the pump 6, or it may connect directly to the reactor vessel 7. The inlet 5 is configured to accept at least one second reactant including at least one oxidant that is introduced into the reactor vessel 7 and thus reacted catalytically in the reactant vessel 7 with the at least one first reagent to form the active disinfection agent. Since the at least one oxidant may include oxygen from air, the inlet 5, may be merely an inlet open to the atmosphere. The inlet 5 may be connected to a gas or liquid reservoir for a suitable oxidant. Reactor vessel 7 contains at least one catalyst that is capable of catalytically effecting a reaction between the at least one alcohol in the first reactant and the at least one oxidant in the second reactant to form the active disinfecting agent.

The reactor vessel 7 that includes at least one catalyst 30 may be within or outside of disinfection vessel 1. Reactor 7 contains the catalyst 30 that converts the feeds from 4 (first reactant including at least one alcohol) and 5 (second reactant that includes at least one oxidant) into an active disinfectant 34. The active disinfection agent 34 may include at least one of aldehydes, carboxylic acids, oxiranes, carbon monoxide, or mixtures thereof. The reactor vessel 7 may be heated or cooled if required. The pressure in the reactor vessel 7 may be controlled. The reactor vessel 7 may be a fixed bed, or monolith, or a fluid bed as known in the art. The reactor vessel 7 may further include within its interior a separate alcohol dehydration vessel 44. The alcohol dehydration vessel 44, if utilized may contain an alcohol dehydration catalyst. If present, the alcohol dehydration vessel 44 may be connected in series or in parallel with the reactor vessel 7.

After the active disinfectant 34 is made in the reactor vessel 7 it is disbursed into the disinfection vessel 1 via outlet 8 where it contacts the material to be disinfected 2 and promotes the disinfection of agents on, or within the material to be disinfected 2. Vessel 1 may be heated, or cooled, to optimal temperature for the disinfection of the target materials 2. Vessel 1 may be pressure-regulated.

The active disinfection agent 34 may be a gas or a liquid or a vapor or a mixture thereof or may be a vapor in equilibrium with a liquid, depending on the particular composition, temperature and pressure of the active disinfecting agent 34. The spent disinfectant 36 (either degraded, or simply unused active disinfection agent 34) is collected via 9 and passed via an optional pump or circulating device 10 to a collection vessel 11. Collection vessel 11 may contain an absorbing medium 42 or may be heated or cooled in order to effectively capture the unreacted disinfecting agent or unreacted first and/or second reagents from the reactor vessel 7 and also any inactivated, disinfected, biological agents. The decontaminated materials from the collection vessel 11 are expelled through vent 12. According to another embodiment, at least a portion of the spent disinfectant 36 from 11 be recycled back to either or both of the disinfection vessel 1 or the reactor vessel 7.

The size of the exemplary device shown in FIG. 1 is not a limiting factor to the utility of the present invention. The device may be small enough to be used in the home, or large enough to be used for hospital or industrial scale applications. Suitable control functionality, known to those skilled in the art of unit automation, can be used to simplify the use of the device.

Device Venting

After sufficient reactant gases, liquids, vapors or mixtures thereof have been utilized for the disinfection, or sterilization, of the biological agents in the device, excess reactants need to be safely removed from the effluent exiting the device. This may be accomplished by any of the methods known in the ethylene oxide industry, for example. Therefore, contained in the device, or external to the device, the exiting gases should pass through a the collection vessel 11 such that the materials released to the external environment pose no safety risk to humans. This collection vessel 11 may include absorbing materials 42, such as activated carbon, solutions of base and bleaching compounds such as sodium hypochlorite. Other non-limiting examples of suitable absorbents or absorbing material 42 are activated alumina; silica gel; silica; zeolites, desiccants; clays; polymeric absorbents such as those used for gas chromatography; superabsorbent polymers, such as sodium polyacrylate, polyacrylamide copolymer, ethylene maleic anhydride copolymer, crosslinked carboxymethylcellulose, polyvinyl alcohol copolymers, cross-linked polyethylene oxide, starch grafted copolymers of polyacrylonitrile; cellulosic absorbent; and combinations thereof. The absorbent 42 may be liquid or solid. The absorbent 42 may be water, or solutions of acid or base in water. For larger applications of the device the spent disinfecting agent gases and/or liquids may be flared (burned), as commonly practiced in the commercial production of ethylene oxide, for example. If the spent disinfecting agent is a gas it may be condensed and/or solubilized before removal from the disinfecting device. If the spent disinfecting agent is a liquid it may be solubilized before removal from the disinfecting device.

The spent disinfecting agent may be catalytically oxidized before removal from the disinfection device. Non-limiting examples of suitable such catalysts may include supported Group VIII metals such as but not limited to platinum, palladium, and ruthenium. The reactor may be a fixed bed, or monolith, or a fluid bed as known in the art.

According to an embodiment, stream 9 shown in FIG. 1 is safe for venting to the living or work space of the device. By safe, it is meant that the composition of stream 9, contains low enough amounts of any regulated materials such that stream 9 is safe as defined by local environmental regulations. Safe may be defined as the expectation that a system does not, under defined conditions, lead to a state in which human life, economics or environment are endangered. Safe may be defined as eliminating or reducing the hazards associated with a set of conditions, in this case exposure to the active disinfecting agent.

Material to be Disinfected

The material to be disinfected may be include one or more of enveloped viruses including SARS-CoV-2 or mutated variants thereof. Other materials that may be disinfected are other viruses, such as those that cause the common cold, influenza; bacteria, such as streptococcus, staphylococcus, MERS and other common airborne, droplet or surface infections including but not limited to: COVID-19; measles morbillivirus, chickenpox virus; Mycobacterium tuberculosis, influenza virus, enterovirus, norovirus; coronavirus, adenovirus, and respiratory syncytial virus.

Active Disinfecting Agent

The active disinfecting agent comprises at least one of C1-C9 aldehydes, C1-C9 carboxylic acids, carbon monoxide, ethylene oxide, C10 or higher aldehydes, C3-C9 ketones, and mixtures thereof. Preferred are lower aldehydes, especially acetaldehyde and/or formaldehyde.

First Reagent Including at Least One Alcohol

The at least one first reagent includes at least one alcohol. Primary, secondary and tertiary alcohols may be used. Primary alcohols are preferred, followed by secondary and then tertiary alcohols. Non-limiting examples of suitable alcohols are C1 to C9 alcohols or mixtures thereof. Particular examples are methanol, ethanol, n-propanol, isopropanol, butyl alcohol and isomers thereof, pentanol and isomers thereof, hexanol and its isomers, heptanol and its isomers, octanaol and isomers thereof, and nonenol and isomers thereof. Mixtures of any and all of these are suitable as well, as are aqueous solutions thereof. Ethanol, and aqueous solutions of ethanol are particular suitable according to certain embodiments.

Second Reagent including at Least One Oxidant

The second reagent includes at least one oxidant. The oxidant may be in the form of a liquid or gas or may be an oxidant dissolved in a suitable solvent. The at least one second reagent may include oxygen. Non-limiting examples of suitable oxidants may be selected from molecular oxygen, oxides of sulfur, oxides of nitrogen and mixtures thereof. Suitable non-limiting examples are air, pure oxygen, $S_2O$, SO, $SO_2$, $SO_3$, $S_7O_2$, $S_6O_2$, $S_2O_2$, $SO_3$ and $SO_4$ and polymeric condensates thereof. Air is a preferred oxidant and it may be ambient air and the air may be wet or it may be dried. Suitable oxides of nitrogen include but are not limited to NO, $NO_2$, $NO_3$, $N_2O$, $N_2O_2$, $N_2O_3$, $N_2O_4$, $N_2O_5$, $N_4O$, $N_4O$, $N(NO_2)_3$ or $N_4O_6$, or mixtures thereof.

According to an embodiment, the first reagent includes at least one alcohol, the second reagent includes oxygen, either molecular or in the form of an oxygen-containing compound and the active disinfecting agent includes at least one aldehyde. According to another embodiment, the first reagent includes ethyl alcohol, the second reagent includes molecular oxygen and the active disinfecting agent includes acetaldehyde.

Catalysts

A non-limiting example of useful catalysts for this transformation are those known to catalyze the epoxidation of ethylene to ethylene oxide. Other catalysts may also be used. While not limited to the present invention, the catalytic transformation of ethanol to acetaldehyde and ethylene oxide can be envisioned via two mechanisms, shown below as reactions (2) and (3). It should be understood that the catalytic conversion of ethanol to acetaldehyde shown below is exemplary only and that other alcohols may be converted to analogous aldehydes using a catalysts. Under the reaction conditions of the present invention these catalysts can convert ethanol to acetaldehyde. This is primarily due to the formation of water, shown in reaction (1) above as well as the reactions (2) and (3) below.

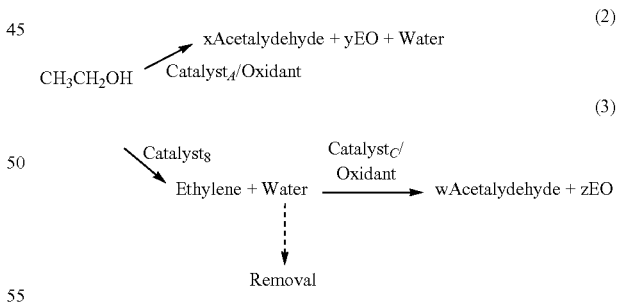

While not limited to these examples, any or a mixture of Catalyst$_A$, Catalyst$_B$, or Catalyst$_C$ compounds and/or compositions thereof that may be useful for catalyzing reaction (2) and/or (3) include Au, Cu, Ag, Mn, Fe, Pr, Nd, Mo, Yb, Zr, Gd, Sm, Ce, Er, W, Ni, Pt, Pd, Ru and combinations thereof on suitable supports such as alumina, silica alumina, ceria or other common supports as known in the art. Other metal catalysts, such as those including Mn, Fe, Pr, Nd or Mo, and supports may be used in the device of FIG. 1 as long as they are effective to the promotion of reactions (2) and/or (3).

Catalysts useful for these reactions may include the above metals and/or compounds including them impregnated on low acidity, high surface area, supports. Suitable supports include alumina ($\alpha$, $\beta$, Y, $\xi$ and $\Omega$), silica, silicon carbide, alkaline earth metals, titanium oxide, tungsten oxide and non-reducible lanthanum oxides. In general, surface areas of the support greater than 5 $m^2/g$ are suitable with preferred surface areas of 100-400 $m^2/g$.

It may also be useful to add alcohol dehydration activity to the catalyst in order to promote reaction (3) shown above. Useful catalysts, or catalytic component for dehydration include y-alumina, silica alumina, silicon aluminum-phosphate and aluminum phosphates. This dehydration function may be part of the oxidation catalyst, added into the reactor bed as a mixture, or be contained in a separate vessel 44 within the reaction vessel of the present invention. According to an embodiment, the dehydration function may be included in a separate vessel. According to an embodiment, the at least one catalyst may further include at least one promoter selected from alkali metals, alkaline earth metals, transition metals or lanthanum group metals. Especially suitable examples of such metals are lanthanum, silver, phosphorous and titanium. The metal may be impregnated on a support including at least one of alumina, silica, silicon carbide, alkaline earth metals, titanium oxide, tungsten oxide, non-reducible lanthanum oxides, or combinations thereof. According to an embodiment, the catalyst may further include at least one of y-alumina, silica alumina, silicon aluminum-phosphate, aluminum phosphates, or mixtures thereof.

According to certain embodiments, promoters such as alkali metals, alkaline earth metals or lanthanum group metals may be included with the catalyst to enhance the reactivity of the alcohols and promote high selectivities to the desired products.

Non-limiting examples of suitable promoters are lanthanum, silver, phosphorous and titanium.

A suitable operating temperature for the catalytic reaction is from 15° C. to 850° C. while 100° C. to 400° C. may be a preferred range for the formation of high selectivities to acetaldehyde. For example, the reaction temperature may be from 25° C. to 300° C., 35° C. to 350° C., 50° C. to 300° C., 75° C. to 350° C., 80° C. to 300° C., 90° C. to 250° C., 120° C-380° C., 150° C. to 400° C., 300° C. to 700° C., 250° C. to 600° C., from 150° C. to 350° C., or from 200° C. to 300° C.

The pressure for the reaction may be from 0.01 to 1,000 atm, or from 0.01 to less than 1 atm. For example, the pressure may be from 0.1 to 1 atm, 0.5 to 0.9 atm, 1 to 10 atm, 0.5 to 1.5 atm, 1 to 1000 atm, 1 to 2 atm, or from 500 to 1000 atm. While air is the preferred oxidant for the catalytic reaction, pure oxygen could also be used or any mixtures thereof. Under the correct application so that safe operating procedures can be maintained, other oxidants such as oxides of sulfur or nitrogen could be used.

While acetaldehyde is the preferred disinfectant of the present invention, any mixtures of other aldehydes or other compounds such as formaldehyde, acetic acid, formic acid, propionic acid, carbon monoxide, ethylene oxide or higher molecular weight aldehydes may be produced in the reactor vessel 7 and are useful in the device of FIG. 1.

Electrogenerative Reactor

Figure 2:
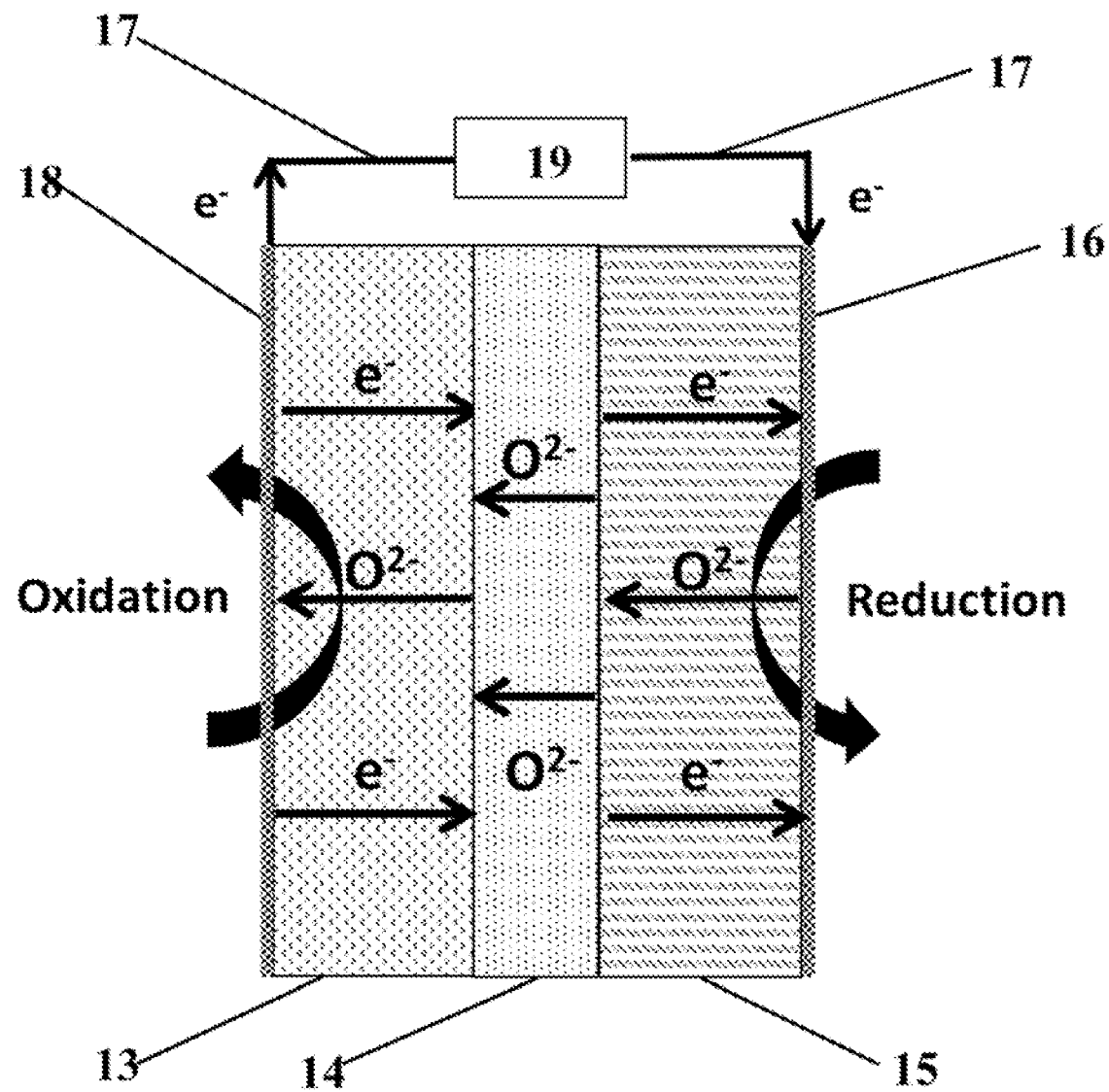
FIG. 2 shows a schematic of an electrogenerative cell in accordance with an embodiment of the invention.

Another embodiment of the current invention is the use of an electrogenerative reactor as the catalytic reactor vessel 7. Such electrogenerative reactors are described in US 2014/0275679 A1, the entire contents of which is incorporated by reference herein for all purposes. An exemplary such reactor is shown in FIG. 2. Referring to FIG. 2, power 19 is applied through the conductor 17 to a cathode plate 16, which promotes the reduction of oxygen to oxygen anion in the cathode membrane 11. Oxygen anion moves through the electron barrier 14, which is intimately associated with the selective oxidation catalyst 18 in the oxidation membrane 13. The oxidation of the components in the reagent stream to form the active disinfection agent occurs in the oxidation membrane 13 and electrons are conducted through an anode plate 15 to complete the power circuit. In this embodiment the effective pressure differential of oxygen between the reduction 15 membrane and oxidation membrane 13 is increased, thus increasing the rate of oxygen anion transfer through the electron barrier 14, which also increases the rate of the formation of the active disinfecting agent. Accordingly, increasing the power 19 applied to the electrogenerative reactor may increase the rate of production of the active disinfecting agent.

A key advantage of the electrogenerative reactor is the ability to actively pump oxygen anion through a membrane, therefore separating the oxygen from air. An additional important benefit is that the voltage 19 applied to the reactor may be varied in order to increase the rate of the conversion of feed to products, thereby allowing for lower temperature operation. It is beneficial to promote these conversions at temperatures less than 800° C. in order to avoid the thermal decomposition of the products. Other suitable temperatures may be 15° C. to 850° C. while 100° C. to 400° C. may be a preferred range for the formation of high selectivities to acetaldehyde. For example, the reaction temperature may be from 25° C. to 300° C., 35° C. to 350° C., 50° C. to 300° C., 75° C. to 350° C., 80° C. to 300° C., 90° C. to 250° C., 120° C-380° C., 150° C. to 400° C., 300° C. to 700° C., 250° C. to 600° C., from 150° C. to 350° C., or from 200° C. to 300° C.

Suitable solid electrolyte materials 4 as shown in FIG. 2 may be any such materials known in the art of solid oxide fuels cells, such as yttrium stabilized zirconia (YSZ) of gadolinium doped ceria (GDC). Most preferred electrolytes will be those that can conduct oxygen ions at temperatures less than 500° C. Therefore, electrolytes based on samarium-neodymium doped ceria (SNDC), erbium-stabilized bismuth oxide (ESB) and didymium-tungsten stabilized bismuth oxide (DWSB) will be useful. Other electrolytes may include the elements yttrium, zirconium, gadolinium, samarium, neodymium, cerium, erbium, praseodymium, bismuth, tungsten, and mixtures, alloys, and compounds thereof with these or other suitable elements.

The catalytic material, 8 of FIG. 2, may be the same as previously described, for the catalytic reactor 5. These materials may be physically mixed or chemically bonded to other materials that promote the transfer of the oxygen anion from the electrolyte to the catalytically active surfaces. Such materials may include electrolytes, as described above, that also comprise Ni, Cu, Pt, Pd, Mo and Ru.

According to an embodiment, the reactor vessel may include a solid oxidation membrane having mixed ionic electronic conductive (MIEC) properties. The solid oxidation membrane may include at least one catalyst disposed on a surface thereof. The solid oxidation membrane may include an oxidation zone configured to receive a feedstream including the first reactant and the second reactant and be further configured to oxidize components of the feedstream to produce the at least one active disinfecting agent.

According to an embodiment, the at least one catalyst may have a cubic crystal lattice structure and a chemical formula of:

$$A_6BO_8;$$

where A is the metal, B is an element that is different than the first metal, and O is oxygen.

According to an embodiment, the catalyst may include at least one of $Mg_6MnO_8$, $Cu_6PbO_8$, $Ni_6MnO_8$, or a mixture thereof.

Also disclosed herein is a method of disinfecting a material using the disclosed disinfection device of claim 1. The method include the following steps:

1) Introducing the material to be disinfected to the disinfection vessel.
2) Introducing the at least one first reagent including at least one alcohol into the reagent vessel.
3) Transferring at least a portion of the at least one first reagent into the reactor vessel from the reagent vessel.
4) Introducing, via the at least one inlet, the at least one second reagent including an oxidant into the reactor vessel.
5) Contacting the at least one first reagent and the at least one second reagent with the at least one catalyst in the reactant vessel to form the active disinfecting agent, which includes at least one of aldehydes, carboxylic acids, oxiranes, carbon monoxide, or mixtures thereof.
6) Dispersing the active disinfecting agent to the disinfection vessel.
7) Contacting the active disinfecting agent and the material to be disinfected to provide a disinfected material and a spent disinfecting agent.
8) Transferring the spent disinfecting agent to the collection vessel.
9) Removing the spent disinfecting agent from the disinfection device via the at least one outlet of the collection vessel.

The method may further include at least one step performed prior to step 9), the step including at least one of burning, catalytically oxidizing, trapping in an adsorbent, liquefying, condensing, or solubilizing the spent disinfecting agent prior to removal from the disinfection device. This step may be performed in the collection vessel.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A disinfection device comprising:
   a disinfection vessel configured to receive material to be disinfected;
   a reagent vessel in fluid communication with the disinfection vessel and having at least one inlet configured to introduce at least one first reagent comprising at least one alcohol into the reagent vessel;
   a reactor vessel in fluid communication with the reagent vessel and the disinfection vessel, the reactor vessel configured to receive at least one catalyst comprising at least one metal selected from transition metals, lanthanide metals and combinations thereof, the reactor vessel having at least one inlet configured to introduce at least one second reagent comprising an oxidant into the reactor vessel; and
   a collection vessel in fluid communication with the disinfection vessel and having at least one outlet;
   wherein, during operation, the at least one first reagent and the at least one second reagent are contacted with the at least one catalyst and reacted in the reactor vessel to form an active disinfecting agent comprising at least one of aldehydes, carboxylic acids, oxiranes, carbon monoxide, ketones, or mixtures thereof, the active disinfecting agent being supplied to the disinfection vessel and contacted with the material to be disinfected to provide a disinfected material and a spent disinfecting agent, the spent disinfecting agent being collected by the collection vessel and removed from the disinfection device via the at least one outlet of the collection vessel.

2. The disinfection device of claim 1, wherein the active disinfecting agent comprises at least one of C1-C9 aldehydes, C1-C9 carboxylic acids, C3-C9 ketones, carbon monoxide, ethylene oxide, C10 or higher aldehydes, or mixtures thereof.

3. The disinfection device of claim 1, wherein the at least one first reagent comprises at least one C1 to C9 alcohol or mixture thereof.

4. The disinfection device of claim 1, wherein the at least one second reagent comprises oxygen.

5. The disinfection device of claim 1, wherein the at least one second reagent comprises at least one oxidant comprising at least one of molecular oxygen, oxides of sulfur, oxides of nitrogen, and mixtures thereof.

6. The disinfection device of claim 1, wherein the first reagent comprises at least one alcohol, the second reagent comprises oxygen and the active disinfecting agent comprises at least one aldehyde.

7. The disinfection device of claim 1, wherein the first reagent comprises ethyl alcohol, the second reagent comprises molecular oxygen and the active disinfecting agent comprises acetaldehyde.

8. The disinfection device of claim 1, wherein the at least one metal comprises at least one of Au, Cu, Ag, Mn, Fe, Pr, Nd, Mo, Yb, Zr, Gd, Sm, Ce, Er, W, Ni, Pt, Pd, Ru, or combinations thereof.

9. The disinfection device of claim 8, wherein the at least one catalyst further comprises at least one promoter comprising at least one of alkali metals, alkaline earth metals, or lanthanum group metals.

10. The disinfection device of claim 8, wherein the metal is impregnated on a support comprising at least one of alumina, silica, silicon carbide, alkaline earth metals, titanium oxide, tungsten oxide, non-reducible lanthanum oxides, or combinations thereof.

11. The disinfection device of claim 8, wherein the catalyst further comprises at least one of y-alumina, silica alumina, silicon aluminum-phosphate, aluminum phosphates, or mixtures thereof.

12. The disinfection device of claim 1, wherein the at least one catalyst further comprises at least one component capable of dehydrating the at least one alcohol.

13. The disinfection device of claim 12, wherein the at least one component capable of dehydrating the at least one alcohol comprises at least one of y-alumina, silica alumina, silicon aluminum-phosphate, aluminum phosphates, and mixtures thereof.

14. The disinfection device of claim 12, wherein the at least one component capable of dehydrating the at least one alcohol is contained in a separate alcohol dehydration vessel within the reaction vessel.

15. The disinfection device of claim 1, wherein the reactor vessel includes a solid oxidation membrane having mixed ionic electronic conductive (MIEC) properties, the solid oxidation membrane comprising the at least one catalyst disposed on a surface thereof, and wherein the solid oxidation membrane includes an oxidation zone configured to receive a feedstream comprising the first reactant and the second reactant and oxidize components of the feedstream to produce the at least one active disinfecting agent.

16. The disinfection device of claim 15, wherein the at least one catalyst has a cubic crystal lattice structure and a chemical formula of:

$A_6BO_8$;

wherein A is the at least one metal, B is an element that is different than the at least one metal, and O is oxygen.

17. The disinfection device of claim 16, wherein the at least one catalyst comprises at least one of $Mg_6MnO_8$, $Cu_6PbO_8$, $Ni_6MnO_8$, or a mixture thereof.

18. The disinfection device of claim 15, wherein the solid oxidation membrane comprises at least one of yttrium stabilized zirconia (YSZ), gadolinium doped ceria (GDC), samarium-neodymium doped ceria (SNDC), erbium-stabilized bismuth oxide (ESB), didymium-tungsten stabilized bismuth oxide (DWSB), or mixtures thereof.

19. The disinfection device of claim 1, wherein the reactor vessel is at a temperature of from 15° C. to 850° C. during the reaction of the first reagent and the second reagent to form the active disinfection agent.

20. The disinfection device of claim 1, wherein the reactor vessel is at a temperature of from 25° C. to 100° C. during the reaction of the first reagent and the second reagent to form the active disinfection agent.

21. The disinfection device of claim 1, wherein the reactor vessel is at a pressure of from 0.01 to 1,000 atm during the reaction of the first reagent and the second reagent to form the active disinfection agent.

22. The disinfection device of claim 1, wherein the reactor vessel is at a pressure of from 0.01 atm to less than 1 atm during the reaction of the first reagent and the second reagent to form the active disinfection agent.

23. The disinfection device of claim 1, wherein a portion of the spent disinfecting agent is recycled to the disinfection vessel.

24. The disinfection device of claim 1, wherein the collection vessel further comprises an absorbent capable of absorbing at least a portion of the spent disinfecting agent prior to removal from the disinfection device.

25. The disinfection device of claim 1, wherein the spent disinfecting agent is burned, catalytically oxidized, trapped in an adsorbent, liquefied, condensed, or solubilized prior to removal from the disinfection device.

26. The disinfection device of claim 1, wherein the material to be disinfected is one or more of enveloped viruses including SARS-CoV-2 or mutated variants thereof.

27. A method of disinfecting a material using the device of claim 1, the method comprising:
    a) introducing the material to be disinfected to the disinfection vessel;
    b) introducing the at least one first reagent comprising the at least one alcohol into the reagent vessel;
    c) transferring at least a portion of the at least one first reagent into the reactor vessel from the reagent vessel;
    d) introducing, via the at least one inlet, the at least one second reagent comprising an oxidant into the reactor vessel;
    e) contacting the at least one first reagent and the at least one second reagent with the at least one catalyst in the reactant vessel to form the active disinfecting agent comprising at least one of aldehydes, carboxylic acids, oxiranes, carbon monoxide, or mixtures thereof;
    f) dispersing the active disinfecting agent to the disinfection vessel;
    g) contacting the active disinfecting agent and the material to be disinfected to provide a disinfected material and a spent disinfecting agent;
    h) transferring the spent disinfecting agent to the collection vessel;
    i) removing the spent disinfecting agent from the disinfection device via the at least one outlet of the collection vessel.

28. The method of claim 27, further comprising at least one step performed prior to step i), the at least one step including at least one of burning, catalytically oxidizing, trapping in an adsorbent, liquefying, condensing, or solubilizing the spent disinfecting agent.

29. The method of claim 28, wherein the at least one step performed prior to step i) is performed in the collection vessel.

* * * * *

UNITED STATES PATENT AND TRADEMARK OFFICE
CERTIFICATE OF CORRECTION

PATENT NO. : 11,648,328 B2
APPLICATION NO. : 17/915012
DATED : May 16, 2023
INVENTOR(S) : John A. Sofranko It is certified that error appears in the above-identified patent and that said Letters Patent is hereby corrected as shown below:

In the Specification

At Column 7, Line 12, -- y-alumina -- should read -- γ-alumina --

At Column 7, Line 28, -- y-alumina -- should read -- γ -alumina --

In the Claims

At Column 10, Line 57, Claim 11. -- y-alumina -- should read -- γ-alumina --

At Column 10, Line 65, Claim 13. -- y-alumina -- should read -- γ -alumina --

Signed and Sealed this
Eighteenth Day of July, 2023

Katherine Kelly Vidal
*Director of the United States Patent and Trademark Office*